US009072655B2

(12) United States Patent
Desai et al.

(10) Patent No.: US 9,072,655 B2
(45) Date of Patent: *Jul. 7, 2015

(54) PROPOFOL FORMULATIONS WITH NON-REACTIVE CONTAINER CLOSURES

(71) Applicant: FRESENIUS KABI USA, LLC, Lake Zurich, IL (US)

(72) Inventors: Neil P. Desai, Pacific Palisades, CA (US); Andrew Yang, Rosemead, CA (US); Sherry Xiaopei Ci, San Marino, CA (US)

(73) Assignee: FRESENIUS KABI USA, LLC, Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,038

(22) Filed: Apr. 22, 2014

(65) Prior Publication Data

US 2014/0224693 A1    Aug. 14, 2014

Related U.S. Application Data

(63) Continuation of application No. 13/909,961, filed on Jun. 4, 2013, which is a continuation of application No. 10/616,709, filed on Jul. 10, 2003, now Pat. No. 8,476,010.

(51) Int. Cl.
| | |
|---|---|
| *A61J 1/05* | (2006.01) |
| *A61J 1/14* | (2006.01) |
| *A61K 9/107* | (2006.01) |
| *A61K 31/05* | (2006.01) |
| *A61J 1/00* | (2006.01) |
| *A61J 1/06* | (2006.01) |

(52) U.S. Cl.
CPC *A61J 1/05* (2013.01); *A61J 1/1412* (2013.01); *A61J 2001/1468* (2013.01); *A61K 9/1075* (2013.01); *A61K 31/05* (2013.01); *A61J 1/00* (2013.01); *A61J 1/06* (2013.01)

(58) Field of Classification Search
None
See application file for complete search history.

(56) References Cited

U.S. PATENT DOCUMENTS

| | | | |
|---|---|---|---|
| 250,448 | A | 4/1950 | Robert et al. |
| 264,909 | A | 8/1953 | Harlan et al. |
| 265,218 | A | 9/1953 | Umbdenstock et al. |
| 4,056,635 | A | 11/1977 | Glen et al. |
| 4,452,817 | A | 6/1984 | Glen et al. |
| 4,798,876 | A | 1/1989 | Gould et al. |
| 5,114,794 | A | 5/1992 | Sudo et al. |
| 5,232,109 | A | 8/1993 | Tirrell et al. |
| 5,439,686 | A | 8/1995 | Desai et al. |
| 5,498,421 | A | 3/1996 | Grinstaff et al. |
| 5,560,933 | A | 10/1996 | Soon-Shiong et al. |
| 5,637,625 | A | 6/1997 | Haynes |
| 5,665,382 | A | 9/1997 | Grinstaff et al. |
| 5,714,520 | A | 2/1998 | Jones et al. |
| 5,731,355 | A | 3/1998 | Jones et al. |
| 5,731,356 | A | 3/1998 | Jones et al. |
| 5,908,869 | A | 6/1999 | Jones et al. |
| 5,916,596 | A * | 6/1999 | Desai et al. .................. 424/489 |
| 5,962,536 | A | 10/1999 | Komer |
| 6,028,108 | A | 2/2000 | George |
| 6,100,302 | A | 8/2000 | Pejaver et al. |
| 6,140,373 | A | 10/2000 | May et al. |
| 6,147,122 | A | 11/2000 | Mirejovsky et al. |
| 6,150,423 | A | 11/2000 | Carpenter |
| 6,177,477 | B1 | 1/2001 | George et al. |
| 6,326,406 | B1 | 12/2001 | De Tommaso |
| 6,362,234 | B1 | 3/2002 | Hendler |
| 6,399,087 | B1 * | 6/2002 | Zhang et al. .................. 424/405 |
| 6,469,069 | B1 | 10/2002 | Mirejovsky et al. |
| 6,576,245 | B1 | 6/2003 | Lundgren |
| 6,749,868 | B1 | 6/2004 | Desai et al. |
| 7,691,904 | B2 | 4/2010 | Marappan et al. |
| 8,476,010 | B2 * | 7/2013 | Desai et al. .................. 435/6.13 |
| 2002/0006442 | A1 | 1/2002 | Mishra et al. |
| 2007/0161601 | A1 | 7/2007 | Desai et al. |
| 2008/0132582 | A1 | 6/2008 | Desai et al. |
| 2009/0017105 | A1 | 1/2009 | Khattar et al. |

FOREIGN PATENT DOCUMENTS

| | | |
|---|---|---|
| EP | 0390244 A1 | 10/1990 |
| WO | 94/18954 | 9/1994 |
| WO | 99/00113 | 1/1999 |
| WO | WO0012043 | 3/2000 |
| WO | 00/54588 A1 | 9/2000 |
| WO | 01/64187 A2 | 9/2001 |
| WO | 02/45709 A1 | 6/2002 |

(Continued)

OTHER PUBLICATIONS

Bauer et al., Pharmazeutische Technologie,: 256-257 (1986).
Farinotti, Annales Francaises d'Anesthesie et de Reanimation., 13:-453-456 (1994).
Jones, Anaesthesia and Intensive Care, 28(5): 587 (Oct. 2000).
Naguib et al., Anesthesiology Abstracts of Scientific Papers Annual Meeting,: 1 (Oct. 13, 2003).
Sautou-Miranda et al., International Journal of Pharmaceutics, 130(2): 251-255 (1996).
Trapani et al., International Journal of Pharmaceutics, 278(1): 91-98 (Jun. 18, 2004).

(Continued)

*Primary Examiner* — Karlheinz R Skowronek
*Assistant Examiner* — Roy Teller
(74) *Attorney, Agent, or Firm* — Baker & Hostetler LLP

(57) ABSTRACT

A container storing an anesthetic is disclosed. The container is sealed by a closure and stores a liquid anesthetic solution. The anesthetic is from 0.1% to 10% by weight of the liquid anesthetic solution. The container is made of a material that is inert to the anesthetic and the closure is made of siliconized rubber or a metal. A concentration of the anesthetic in a liquid anesthetic solution stored in the container following a predetermined time period is at least 93% of a concentration of the anesthetic in a liquid anesthetic solution before the liquid anesthetic solution is stored in the container.

21 Claims, No Drawings

(56) References Cited

FOREIGN PATENT DOCUMENTS

| WO | WO 02/45709 | * | 6/2002 |
|---|---|---|---|
| WO | 2004/052401 A2 | | 6/2004 |
| WO | 2010/138170 A2 | | 12/2010 |

OTHER PUBLICATIONS

West Furotec Barrier Film,: 1-2 (Dec. 3, 2003), [http://web.archive.org/web/20031203023630/http://www.westpharma.com/products/flurotec.asp].
Website, "Melagatran—Compound Summary (CID 183797)", Nov. 15, 2010, Publisher: http://pubchem.ncbi.nlm.nih.gov/summary/summary.cgi?cid=183797.
Website, "Propofol—Substance Summary (SID 9726)", Nov. 15, 2010, Publisher: http://pubchem.ncbi.nlm.nih.gov/summary/summary.cgi?cid=9726.
International Searching Authority, "International Search Report and Written Opinion for PCT/US04/020923", Aug. 18, 2005, Publisher: European Patent Office, Published in: EP.
Arduino, et al., "Microbial Growth and Endotoxin Production in the Intravenous Anesthetic Propofol","Infection Control and Hospital Epidemiology", Sep. 1991, pp. 535-539, vol. 12, No. 9.
Baker, et al., "Sulfite Supported Lipid Peroxidation in Propofol Emulsions", "Anesthesiology", Nov. 2002, pp. 1162-1167, vol. 97, No. 5.
Benz, et al., "Electrical Capacity of Black Lipid Films and of Lipid Bilayers Made from Monolayers", "Biochimica et Biophysica Acta", 1975, pp. 323-334, vol. 394.
De Sommer, et al., "Abstract—A comparative study on the effects of propofol in emulsion and Intralipid on fat metabolism", "Acta Anaesthesiol Belg", 1990, pp. 133-138, vol. 41, No. 2.
Eddleston, et al., "The effect on serum lipid concentrations of a prolonged infusion of propofol-hypertriglyceridaemia associated with pro", "Intensive Care Med", 1991, pp. 424-426, vol. 17.
Gottardis, et al., "Effect of prolonged sedation with propofol on serum triglyceride and cholestrerol concentrations", "Br. J. Anaesth. ", 1989, pp. 393-396, vol. 62.
Langevin, Paul B., "Propofol Containing Sulfite—Potential for Injury", "Chest", Oct. 1999, pp. 1140-1141, vol. 116, No. 4.
Lindholm, M., "Abstract—Critically ill patients and fat emulsions", "Minerva Anestesiol", Oct. 1992, pp. 875-879, vol. 58, No. 10.
Mayhew, et al, "Characterization of liposomes prepared using a microemulsifier", "Biochimica et Biophysica Acta", 1984, pp. 169-174, vol. 775.
Mirejovsky, et al, "Pharmaceutical and antimicrobial differences between propofol emulsion products", "Am J Health-Syst Pharm", Jun. 15, 2000, pp. 1174-1177, vol. 57.
Sosis, et al, "Growth of *Staphylococcus aureus* in Four Intravenous Anesthetics", "Anesth Analg", 1993, pp. 766-768, vol. 77.
Adachi et al., "A Case of Coring on Using a 1% Diprivan Vial," Masui, 50: 635-6 (2001) (Abstract only).
Anschel, "General Guidelines for the Selection and Processing of Rubber Closures for Parenteral Products," Bull. Parenteral Drug Assoc., 31(6): 302-08 (1977).
Barber, "Sources of Particulate Matter in Pharmaceutical and Medical Products," Liquid- and Surface-Borne Particle Measurement Handbook: 637-. J.Z. Knapp et al., ed. (1996).
Barber, "Sources and Characteristics of Contaminant Particles," Control of Particulate Matter Contamination in Healthcare Manufacturing: 27-59 (2000).
Colas et al., "Silicones in Pharmaceutical Applications," Dow Corning Healthcare Industries (2001).
Colas et al., "Silicones in Pharmaceutical Applications," Dow Corning Healthcare Industries (2006).
"Common Clinical Questions," Diprivan website (Aug. 3, 2001).
"Diprivan," Physicians' Desk Reference: 2168 (1991).
"Diprivan," Physicians' Desk Reference: 2328 (1994).
FDA, Draft Guidance for Industry Stability Testing of Drug Substance and Drug Products (Jun. 1998).
FDA, Guidance for Industry: Container Closure Systems for Packaging Human Drugs and Biologics (May 1999).
Frampton et al., "Sterile Products and the Role of Rubber Components" in Pharmaceutical Packaging Technology: 499- D.A. Dean et al. eds. (2000).
Mundry et al., "The Fate of Silicone Oil During Heat-curing Glass Siliconization—Changes in Molecular Parameters Analyzed by Size Exclusion and High Temperature Gas Chromatography," PDA Journal of Pharmaceutical Science and Technology, 54(5): 383-397 (2000).
Parsons et al., "No Loss of Undiluted Propofol by Sorption into Administration Systems," Pharm. Pharmacol. Commun., 5: 377-381 (1999).
Pavanetto et al., "Particulate Contamination from Siliconized Rubber Stoppers," Intl. J. Pharmaceutics, 74: 175-181 (1991).
Rifkin, "Panel Discussion: Siliconization of Parenteral Packaging Components. I. Siliconization: as Applied to Containers and Closures," Bull. Parenteral Drug Assoc., 22(2): 66-69 (1968).
Reuter et al., "Syringe Siliconization," TechnoPharm, 2(4): 238-244 (2012).
Smith et al., "New Process for Treatment of Parenteral Closures," Bull. Parenteral Drug Assoc., 30(2): 53-63 (1976).
Smith et al., "Siliconization of Parenteral Drug Packaging Components," J. Parenteral Sci. & Tech., 42(4S): S1-S13 (1988).
Colas and Aguadisch, "Les silicones dans les applications pharmaceutiques," Chimie Nouvelle, 15(58): 1779 (1997).
Entry for Diprivan® in the Physician's Desk Reference, 51st Edition, 1997, pp. 341, 2939-2945 (9 pages).
English-Language Translation of R. Farinotti, "Physio-chemical Interactions and Storage of Diprivan®," Ann. Fr. Anesth. Reanim., 1994 (4 pages).
Han et al., "Physical properties and stability of two emulsion formulations of propofol," Int'l J. of Pharmaceutics, 215 (2001) 207-220 (14 pages).
West Technical Support Bulletin 1999/013, "Evaluating B2-Coating as an Alternative to Silicone Oil," Jan. 26, 1999 (1 page).
West Technical Report 20001026, "B2-Coating Quantitative Particle Analysis," Nov. 15, 2000 (4 pages).
Webster's Third New International Dictionary (2002), p. 2118 (3 pages).
Hawley's Condensed Chemical Dictionary (13th ed. 1997), pp. 997-998 (4 pages).
Dutch Diprivan® Registration, 10 mg SmPC RVG 25809 (2000) (13 pages).
English-Language Translation of Dutch Diprivan® Registration, 10 mg SmPC RVG 25809 (2000) (14 pages).

* cited by examiner

PROPOFOL FORMULATIONS WITH NON-REACTIVE CONTAINER CLOSURES

CROSS-REFERENCE TO RELATED APPLICATIONS

This application is a continuation of U.S. patent application Ser. No. 13/909,961, filed Jun. 4, 2013, which is a continuation of U.S. patent application Ser. No. 10/616,709, filed Jul. 10, 2003, and now U.S. Pat. No. 8,476,010, the disclosures of which are incorporated by reference in their entirety.

FIELD OF THE INVENTION

The invention generally pertains to pharmaceutical formulations of propofol, an intravenous anesthetic with enhanced microbial inhibition. More particularly, the invention pertains to propofol formulations that are stored in containers having non-reactive, or inert closures.

BACKGROUND OF THE INVENTION

Propofol (2,6-Diisopropylphenol) is a well-known and widely used intravenous anesthetic agent. For example, in intensive care units (ICU) where the duration of treatment may be lengthy, propofol has the advantage of a rapid onset after infusion or bolus injection plus a very short recovery period of several minutes, instead of hours.

Propofol is a hydrophobic, water-insoluble oil. To overcome the solubility problem, it must be incorporated with solubilizing agents, surfactants, solvents, or an oil in water emulsion. There are a number of known propofol formulations, such as disclosed in U.S. Pat. Nos. 4,056,635, 4,452, 817 and 4,798,846 all of which are issued to Glen and James.

Propofol compositions have been the subject of several patents. Typically, propofol compositions comprise 1-2% by weight propofol, 1-3% or 10-30% of a water immiscible solvent such as soybean oil, 1.2% of egg lecithin as a surfactant, and 2.25% glycerin as a tonicity agent. Variation in pH and/or addition of other components allows for various advantages and uses. For example, Hendler (U.S. Pat. No. 6,362,234) uses propofol esters (100 mg-3 gm) in combination with anti-migraines to make aqueous, solid and other non-aqueous compositions for internal and transdermal delivery, for the treatment of migraines. De Tommaso (U.S. Pat. No. 6,326,406) discloses a composition of pH 4.5-6.5 comprising 10 mg/ml propofol, 25-150 mg/ml bile salt, a lecithin, and preparation with substantially no oxygen. Mixing propofol with bile acid produces a clear formulation and allows for easy detection of foreign particles. For veterinary applications, benzyl alcohol and phospholipid free composition comprising from 1-30% by weight propofol, wherein the aqueous solution is sterile filtered has been used to anesthetize animals (Carpenter, U.S. Pat. No. 6,150,423). Higher percentages of propofol allow for administration of smaller quantities.

To prevent microbial growth, various components and methods of preparation have been discussed. For example, Mirejovsky, et al., disclose compositions of pH 4.5-6.4 with less than 1% sulfites and 1-2% by weight propofol (U.S. Pat. Nos. 6,469,069 and 6,147,122); George, et al., disclose 0.15-0.25% tromethamine with 1-2% by weight propofol and pH 8.5-10 (U.S. Pat. No. 6,177,477); 0.005% EDTA with 1-2% by weight propofol and pH 6-8.5 has been used by Jones, et al., (U.S. Pat. Nos. 5,714,520, 5,731,355, and 5,731,356); George (U.S. Pat. No. 6,028,108), discloses compositions with 0.005-0.1% pentetat that are 1-2% by weight propofol and pH 6.5-9.5. Likewise, lowering pH ranges (pH 5-7), using egg lecithin (0.2-1%) and soybean oil (1-3%), without preservatives and 0.1-6% propofol by weight (Zhang, et al., U.S. Pat. No. 6,399,087), and lowering concentrations of soybean oil (1-3%) to produce stable emulsions and reducing nutrients with 1% propofol by weight (Pejaver, et al., U.S. Pat. No. 6,100,302), are said to provide protection against microbial contamination. Reducing lipid concentrations also reduces the chances of fat overload and is ideal for use when administered over extended time periods. In addition, compositions devoid of fats and triglycerides, with 3% w/v propofol (Haynes, U.S. Pat. No. 5,637,625) are said to be useful for sedation over extended periods of time.

There are two major problems associated with the formulations described in the above patents: (1) the risk of microbial contamination due to the high nutrient content and lack of antimicrobial preservatives. Studies by Arduino, et al., 1991; Sosis & Braverman, 1993; and PDR, 1995, have shown that a propofol emulsion formulated without preservatives will grow bacteria and present a risk of bacterial contamination; (2) Hyperlipidemia in patients undergoing long-term ICU sedation due to a large amount of fat content. Studies have shown that triglyceride overload can become a significant problem when a 1% propofol/10% soybean oil emulsion is used as the sole sedative for a long period of ICU sedation by Gottardis, et al., 1989; DeSoreruer, et al., 1990; Lindholm, 1992; and Eddieston, et al, 1991.

To solve the problem of bacterial contamination of propofol emulsion, the following patented formulations of propofol have been developed:

| Patent No. | Inventor | Issued |
| --- | --- | --- |
| 5,637,625 | Duncan H. Haynes | 10 Jun. 1997 |
| 5,714,520 | Christopher B. J., et al. | 3 Feb. 1998 |
| 6,028,108 | Mary M. G. | 22 Feb. 2000 |
| 6,100,302 | Satish K. P., et al. | 8 Aug. 2000 |
| PCT 99/39696 | Mirejovsky D., et al. | 12 Aug. 1999 |
| PCT 00/24376 | Mary T., et al. | 4 May 2000 |

The formulations described in U.S. Pat. No. 5,714,520 is sold as DIPRIVAN® and comprises a sterile, pyrogen-free emulsion containing 1% (W/v) propofol in 10% (w/v) soybean oil. The formulation also contains 1.2% (w/v) egg lecithin as a surfactant, 2.25% (w/v) glycerol to make the formulation isotonic, sodium hydroxide to adjust the pH, and EDTA 0.0055% (w/v) as a preservative. This formulation prevents no more than a 10-fold increase against gram negative (such as *Pseudomonas aeruginosa* and *Escherichia coli*) and gram positive (*Staphylococcus aureus*) bacteria, as well as yeast (such as *Candida albicans*) over a twenty-four hour period. However, EDTA, which is a metal ion chelator, removes cations like calcium magnesium and zinc. This can be potentially dangerous to some patients with low calcium or other low cation levels, and especially critical for ICU patients.

In U.S. Pat. No. 6,028,108 the propofol formulation contains pentetate 0.0005% (w/v) as a preservative to prevent microbial contamination. Pentetate is a metal ion chelator similar to EDTA and therefore represents the same potential danger.

The formulation described in W.O. Patent No. 99/39696, is generic propofol containing 0.25 mg/mL sodium metabisulfite as a preservative to prevent microbial growth. At 24 hours there is no more than a one log increase. Recently, P. Langevin, 1999, has expressed concern that generic propofol containing 0.25 mg/mL sodium metabisulfite, infused at a rate of 50 ug/kg/min, will result in sulfite administration approaching the toxic level (i.e., near the LD50 for rats) in about 25 hours.

Particularly, the addition of sulphites to this drug is worrisome for the potential effects to the pediatric population and for sulphur allergy to the general population. In a June 2000 letter, the manufacturer of metabisulphite-containing propofol emulsion (Gensia Sicor) stated that discoloration and a reduction in pH occur when the product is exposed to air and that both phenomena are caused by the oxidation of sodium metabisulphite Mirejovsky D. Ghosh M. Reply. (Pharmaceutical and antimicrobial differences between propofol emulsion products) (Am J Health-Syst Pharm. 2000: 57:1176-7). Results show that the yellowing of the commercial metabisulphite-containing propofol emulsion is an oxidized form of propofol dimer quinine which is lipid soluble. (U.S. Pat. No. 6,399,087). Recent data also support pro-oxidant activity by the sulfite anion resulting in propofol dimerization and lipid peroxidation (Baker et al., Anesthesiology, 96, A472, 2002).

The formulation described in PCT W.O. Patent No. 00/24376 is a formulation having an antimicrobial agent, which is a member selected from the group consisting of benzyl alcohol and sodium ethylenediamine tetraacetate, benzethonium chloride; and benzyl alcohol and sodium benzoate. The formulation contains EDTA, which was mentioned as related to the side effect above. Benzyl alcohol is linked to adverse reactions reported by Evens and Lopez-Herce, et al. The formulation may be unsafe upon administration, particularly to those patients who need an extended period of ICU sedation.

The formulation described in U.S. Pat. No. 5,637,625 is of phospholipid-coated microdroplets of propofol, containing 6.8% propofol with no soybean oil. However, it is believed that this formulation may increase injection site pain to an unacceptable level during administration.

The formulation described in U.S. Pat. No. 6,100,302 is an emulsion of propofol that contains 1-3% of soybean oil to prevent against accidental microbial contamination during long-term IV infusions due to an increased availability of propofol.

Egg lecithin is mainly used in pharmaceutical products as a dispersing, emulsifying, and stabilizing agent. The lecithin is also used as component of enteral and paranteral nutrition formulations, Arthur H. Kibbe, 2000.

It has been also found that in this invention a propofol formulation containing a reduced amount of egg lecithin results in a significant increase in the ability to be antimicrobial. The soybean oil is also source of nutrition to support the microbial growth.

Thus, it has been found that the preservative-free, optimized propofol formulation of this invention addresses the prior art problems to the point where the problems are eliminated or at the least are substantially reduced.

It has now been discovered that the propofol in propofol formulations with reduced oil content is degraded when stored in a container with a closure that is not inert to propofol. The problem of propofol degradation encountered was quite unexpected as closures sealed with a rubber stopper or the like are known. For example, U.S. Pat. No. 6,576,245 points out that primary packages such as vials, bottles, cartridges, prefilled syringes and the like are typically sealed by a rubber stopper or plunger. U.S. Pat. No. 6,576,245 further expresses a preference for a rubber material containing bromobutyl instead of chlorobutyl to improve the stability of low molecular weight thrombin inhibitors in solution. Heretofore, however, the art has not understood that the propofol in propofol formulations is susceptible to degradation due to exposure to the closure for the container. The failure of the art to recognize the effect of the container closure on propofol degradation, it is believed, is due to the fact that the commercially available propofol formulation DIPRIVAN® comprises 10% (w/v) soybean oil. Applicants have found that at the relatively high volume of soybean oil used in prior art formulations, the soybean oil apparently protects propofol from degradation. However, at oil contents (and/or propofol solvent contents) lower than about 10% (w/v), degradation of propofol has been found to occur if the container closure is not inert or non-reactive to propofol.

DISCLOSURE OF THE INVENTION

Accordingly, the present invention in one of its embodiments provides a sterile formulation of propofol for parenteral administration containing a reduced amount of egg lecithin and soybean oil triglycerides. The formulation is preferably comprised of an oil in water emulsion with a mean particle size of from about 100 to about 300 nanometers in diameter, in which the propofol is dissolved in a water-immiscible solvent such as soybean oil, and stabilized by a surfactant such as egg lecithin. The composition preferably has a pH in the range of from about pH 5 to about pH 8. The low amount of lecithin and soybean oil in the formulation offers a number of advantages. In other embodiments of the invention, the composition includes protein, such as albumin. The presence of protein such as albumin in the propofol formulation is also advantageous. The advantages of the formulations in accordance with the embodiments of the invention include:

(1) eliminating preservatives, such as EDTA that can result in zinc loss due to chelation, (2) providing formulations with excellent exhibition of antimicrobial activity compared to formulations with higher amount of lecithin and oil solvent emulsion containing preservatives, and (3) a reduced risk of hyperlipidemia in patients.

Further, the presence of protein, such as albumin in the propofol formulation reduces the propofol-induced pain on injection. Pain reduction is due to binding of free propofol with albumin and consequent reduction of the free propofol injected. It has also been found that the protein, and in particular, albumin, assists in forming the stabilizing layer at the interface of the so-called oil phase and aqueous phase of the emulsion. Further, the use of protein provides for compositions which do not include a water-immiscible solvent for propofol or a surfactant or both. Thus, in one embodiment of the invention, there is provided a sterile pharmaceutical composition for parenteral administration of propofol, in which the composition comprises propofol, an aqueous phase and protein, such as albumin.

The propofol formulations of the present invention have no more than a 10-fold increase in the growth of each of *Pseudomonas aeruginosa, Escherichia coli, Staphylococcus aureus* and *Candida albicans* for at least 24 hours after adventitious, extrinsic contamination.

In a further embodiment of the present invention, the propofol composition is stored in a container that is inert or non-reactive and that has an inert or non-reactive closure, such that the container and closure do not cause significant degradation or loss in potency of the propofol formulation. Thus, by way of illustration, the degradation or loss of potency of propofol should be such that the propofol composition meets regulatory safety and efficacy standards. As a result, impurity levels, levels of degradation products, and potency loss are within accepted regulatory limits. The closure can itself be inert or non-reactive, or the closure can be coated with a suitable coating material to make it non-reactive or inert.

These and other objects and advantages of the present invention will become apparent from the subsequent detailed description of the preferred embodiment and the appended claims.

DETAILED DESCRIPTION OF THE INVENTION

The invention in one of its embodiments is a sterile pharmaceutical composition for parenteral administration comprised of an oil-in-water emulsion, in which propofol is dissolved in a water-immiscible solvent, preferably soybean oil, and stabilized by a surfactant, preferably egg lecithin. The composition further comprises a reduced amount of egg lecithin and soybean oil to inhibit microbial contamination during IV infusions over a period of time. In other embodiments of the invention, water immiscible solvents can also be used. The composition preferably comprises protein, such as albumin which binds free propofol to reduce the pain on injection. In another embodiment, the invention comprises compositions of propofol having no oil. In this embodiment, the composition also preferably comprises protein, such as albumin.

An oil-in-water emulsion is meant to be a distinct, two-phase system that is in equilibrium and in effect, as a whole, is kinetically stable and thermodynamically unstable. Thus, as used herein, the aqueous phase refers generally to the phase which includes water or water of injection with or without other water soluble or water miscible components, and the oil phase refers to the phase that includes propofol. The propofol may be present neat, or with a solvent oil or other propofol miscible component.

Prevention of a significant growth of microorganisms is meant to be growth of microorganisms, which is preferably no more than a one log increase following extrinsic contamination generally found in treatment settings such as ICU's and the like. For purposes of this definition, the contamination is commonly about 50-200 colony forming units/ml at a temperature in the range of 20-25° C.

The composition of the present invention typically comprises from 0.1% to 10% by weight of propofol, and, more preferably from 1 to 5% propofol. Preferably, the composition comprises 1%, 2% or 5% propofol. All references herein to weight percent are meant to be weight percent by volume of the composition.

The water miscible solvent or the water-immiscible solvent is present in an amount that is preferably from 0 to 10% by weight of the composition, and more preferably from 1 to 6% by weight of the composition for the formulation containing 0.5-5% propofol. Also preferred are compositions that contain no water-immiscible solvents so that the propofol is present neat.

The oil-in-water emulsion can be prepared by using neat propofol or by dissolving propofol in a solvent, and preparing an aqueous phase containing water of injection and optionally a surfactant, protein and other water-soluble ingredients, and then mixing the oil with the aqueous phase. The crude emulsion is homogenized under high pressure to provide an emulsion.

A wide range of water-immiscible solvents can be used in the composition of the present invention. Typically, the water-immiscible solvent is a vegetable oil, for example, soybean, safflower, cottonseed, corn, coconut, sunflower, arachis, castor sesame, orange, limonene or olive oil. Preferably, the vegetable oil is soybean oil. Alternatively, the water-immiscible solvent is an ester of a medium or long-chain fatty acid, for example a mono-, di-, or triglyceride, or is a chemically modified or manufactured palmitate, glyceral ester or polyoxyl, hydrogenated castor oil. In a further alternative, the water-immiscible solvent may be a marine oil, for example cod liver or other fish-derived oil. Suitable solvents also include fractionated oils, for example, fractionated coconut oil, or modified soybean oil. Furthermore, the composition of the present invention may comprise a mixture of two or more of the above water-immiscible solvents. Water-miscible solvents may also be utilized. Thus, for example, suitable solvents include chloroform, methylene chloride, ethyl acetate, ethanol, tetrahydrofuran, dioxane, acetonitrile, acetone, dimethyl sulfoxide, dimethyl formamide, methylpyrrolidinone, and the like. Additional solvents contemplated for use in the practice of the present invention include C1-020 alcohols, C2-C20 esters, C3-C20 ketones, polyethylene glycols, aliphatic hydrocarbons, aromatic hydrocarbons, halogenated hydrocarbons and combinations thereof. Certain solvents that are volatile or non-volatile may be utilized but may be desirably removed in the final parenteral preparation to acceptable levels for parenteral administration. In addition mixtures of any two or more of the above solvents are also acceptable.

The composition of the present invention can comprise a pharmaceutically acceptable surfactant to provide a stable emulsion. The amount of the surfactant present in the composition will vary depending on the amount of solvent for the propofol. For example, the surfactant is suitably present in an amount that is no more than 1% by weight of the composition for a formulation that contains 1 to 6% of water-immiscible solvent, more preferably the amount of surfactant is 0.2 to 1.0% by weight of the composition, and even more preferably the amount of surfactant is 0.3-0.66% by weight of the composition. For a formulation that contains 6 to 10% of water-immiscible solvent, a suitable amount of surfactant is no more than 5% by weight of the composition, and preferably is 0.5 to 3% by weight of the composition, and more preferably is 0.8-1.2% by weight of the composition. Acceptable range of surfactant concentration is 0.1-5%, more preferably, 0.2-3% and most preferably 0.3-0.8%. Suitable surfactants include synthetic non-ionic surfactant such as ethoxylated ethers and esters such as Tween 80 and Tocopherol polyethylene glycol stearate (Vitamin E-TPGS), and polypropylene-polyethylene block co-polymers, and phosphatides or lecithins, for example naturally occurring phosphatides such as egg and soya phosphatides, or egg and soya lecithins and modified or artificially manipulated phosphatides (for example those prepared by physical fractionation and/or chromatography), or mixture thereof. Preferred surfactants are egg and soya phosphatides. Most preferred is egg lecithin.

It is well recognized that a surfactant can stabilize an emulsion by forming a stabilizing layer at the surface of the oil phase or droplet phase of the emulsion. The presence of protein such as albumin in the composition of the present invention has been found to stabilize the emulsion, with and without surfactant present in the composition. For propofol compositions of embodiments of the invention which contain protein, such as albumin as well as surfactant, it has been found that the emulsions are stabilized by the presence of albumin as well as the surfactant in the stabilizing layer at the surface of the oil phase or droplet phase of the emulsion. For propofol compositions of embodiments of the invention which contain protein such as albumin, but no surfactant, it has also been found that albumin is present on the droplets of the oil phase of the emulsion and is included in the stabilizing layer. The total albumin measured in the droplet phase of the emulsion was at least 0.5-10% of the total albumin in the formulation. Thus the stabilizing layer in such invention formulations comprises both the surfactant (e.g., lecithin) as well as the protein (albumin). The mean size of the droplets typically is in the range from about 20 nanometers to about 1000 nanometers, desirably from about 50 nanometers to about 500 nanometers, and more desirably from about 100 to about 300 nanometers.

Proteins contemplated for use as stabilizing agents or for purposes of binding free propofol to reduce pain in accordance with the present invention include albumins, globulins, immunoglobulins, lipoproteins, caseins, insulins, hemoglobins, lysozymes, alpha.-2-macroglobulin, fibronectins, vitronectins, fibrinogens, lipases, and the like. Proteins, peptides, enzymes, antibodies and combinations thereof, are contemplated for use in the present invention. Preferred concentrations of proteins are 0.01-5%, more preferably, 0.1-3% and most preferably 0.2-1%. The preferred protein is albumin, most preferably human albumin or recombinant human albumin.

The composition of the present invention is suitably formulated to have a pH range of 4.5 to 9.0, preferably pH 5.0 to pH 7.5. A pH range of 6-8 is also suitable. The pH can be adjusted as required by means of a suitable pH modifier, that is, a component that can be used to adjust pH to the desired range and yet is suitable for parenteral administration. The pH of the composition can be adjusted by the addition to the formulation of the pH modifier. It will also be understood that the water of injection can include the pH modifier so the resulting composition has the desired pH range. Thus, by way of example, the pH modifier can be added to the water of injection to achieve the desired pH, and the pH-modified water of injection can then be used to make the formulation. The pH adjustment is a matter of processing choice. Suitable pH modifiers include alkali metal salts, such as sodium hydroxide, and acids, including mineral acids such as hydrochloric acid and organic acids.

The composition of the present invention may be made isotonic with blood by incorporation of a suitable tonicity modifier, for example glycerin.

The composition of the present invention comprises a pharmaceutically acceptable carrier. The carrier is preferably a pyrogen-free water or water for injection U.S.P.

The present invention's composition is a sterile aqueous formulation and is prepared by standard manufacturing techniques using, for example, aseptic manufacture, sterile filtration or terminal sterilization by autoclaving.

The compositions of the present invention are useful as anesthetics, which include sedation, induction and maintenance of general anesthesia. Accordingly, in another aspect, the present invention provides a method of producing anesthesia (including sedation, induction and maintenance of general anesthesia) in a warm-blooded animal, including humans.

Producing anesthesia comprises administering parenterally a sterile, aqueous pharmaceutical composition which comprises an oil-in-water emulsion in which neat propofol or propofol in a water-miscible or a water-immiscible solvent is emulsified with water and a surfactant.

Typically, dosage levels of propofol for producing general anesthesia are from, about 2.0-2.5 mg/kg for an adult. Dosage for maintenance of anesthesia is generally about 4-12 mg/kg/hr. Sedative effects may be achieved with, for example, a dosage of 0.3-4.5 mg/kg/hr. Dosage levels of propofol for producing general anesthesia, induction and maintenance, and for producing a sedative effect, may be derived from the substantive literature and may be determined by one skilled in the art to suit a given patient and treatment regime.

Accordingly, in one aspect, the present invention provides an optimized formulation that comprises a sufficiently low amount of egg lecithin which is reduced from the industry standard of 1.2% by weight to about 0.4% by weight. In another aspect, the present invention provides a formulation that comprises a low amount of soybean oil, which is decreased from the industry standard of 10% by weight to 1-6% by weight, preferably 3% by weight. In yet another aspect, the present invention provides a formulation with a pH range of pH 5.0-8.5, preferably pH 6.0 to 8.0. A pH 5.0 to 7.5, or pH 5.0 to 7.0 is also suitable. Variations of pH, such as pH 7.0 to 8.5, are equally suitable.

In accordance with the present invention several advantages have been found, which include, no more than a ten-fold increase in the growth of microorganism, such as S. aureus, E. coli, P. aeruginosa and C. albicans for at least 24 hours, a reduction in the risk of hyperlipidemia, elimination of EDTA that may cause zinc loss and a reduction in the risk of pain due binding of free propofol with albumin.

The compositions of the present invention preferably are prepared by a process which is carried out under an inert atmosphere, since propofol is known to be sensitive to oxidation. Typically the process for preparing the sterile emulsion for parenteral administration involves preparation of the aqueous phase and preparation of the oil phase (in any order) and mixing the oil phase with the aqueous phase. In the preferred method of making the propofol formulations of the invention, the aqueous phase is prepared by adding glycerin into water for injection. Then other ingredients, if used, are added. For example, if albumin is included in the formulation, albumin is added to the aqueous phase, that is, to the water of injection. The oil phase can be neat propofol or propofol added to a solvent for propofol. For example, the solvent can be a water miscible solvent, such as methanol, or a water-immiscible solvent, such as soybean oil and/or other organic solvent, as well as mixtures of solvents. The composition can also include a surfactant, and if surfactant is included in the composition, it can be added to either the aqueous phase or the oil phase depending on the surfactant used. In a preferred method, surfactant, such as lecithin, is added to the oil phase and stirred until dissolved at about 20° C.-60° C. The oil phase is added to the aqueous phase, and mixed to form the crude emulsion. In a preferred embodiment, the aqueous phase includes human serum albumin. The crude emulsion is homogenized at high pressure until the desired emulsion size is reached, and the pH is adjusted, if necessary. The emulsion is then sterile filtered to form the final sterile emulsion, under inert atmosphere, preferably into a holding vessel. Sterile containers or vials can be filled from the sterile holding vessel, also under inert atmosphere.

In accordance with a further embodiment of the invention, the propofol formulation is stored in a container that includes a closure, and the closure is inert or non-reactive with respect to propofol, such that the closure does not cause degradation or loss in potency of propofol formulations. The closure can itself be inert or non-reactive, or the closure can be coated with a suitable coating material to make it non-reactive or inert. The container is also preferably inert or non-reactive and/or the container is treated to be inert or non-reactive. The invention is particularly advantageous for storing propofol formulations that are susceptible to propofol degradation or potency loss. For example, the invention is advantageous for storing propofol formulations that contain less than about 10% (w/v), water-immiscible solvent for propofol, such as oil, preferably less than 7% (w/v) water-immiscible solvent and more preferably less than 4% (w/v) water-immiscible solvent. Thus, it will be appreciated by those skilled in the art that the present invention can be used for any propofol formulation that contains insufficient propofol solvent to protect the propofol from degradation or loss of potency. For example, the propofol compositions described herein, as well as the sterile pharmaceutical propofol composition described in U.S. Pat. No. 5,637,625, the disclosure of which is incorporated herein by reference, is, in accordance with the present invention, stored in a container that has an inert or non-reactive closure. The '625 patent describes formulations of propofol as a phospholipid-coated microdroplet substantially completely devoid of fats or triglycerides. The phospholipid-coated microdroplets at about 0.1 µm diameter droplet of drug in the oil state, coated with a stabilizing monolayer of phospholipid are described in U.S. Pat. Nos. 4,622,219 and 4,725,442, the disclosures of which are hereby incorporated by reference.

The coating material of the propofol microdroplet can be chosen from the lipids described in U.S. Pat. No. 4,725,442, cols. 5-7, particularly the phospholipids described in Class A, B and C. Additionally, the microdroplet can be coated by certain mono-glycerides capable of forming oriented monolayers and bilayers in the presence of decane (Benz et al. Biochim. Biophys. Acta 394:323-334, 1975). Examples of useful mono-glycerides include, but are not limited to, the following:
1-monopalmitoyl-(rac)-glycerol (Monopalmitin)
1-monocaprylol-(rac)-glycerol (Monocaprylin)
1-monooleoyl-(rac)-glycerol (C18:1, cis-9) (Monoolein)
1-monostearyl-(rac)-glycerol (Monostearin)
Phosphatidylcholine (lecithin) is the most useful example.

The preferred method of preparing propofol microdroplets described in the '625 patent on the laboratory scale is sonication with a probe sonicator. For industrial scale production, Microfluidization® (Microfluidics Corp., Newton, Mass. 02164) is preferred. The apparatus is described by Mayhew et al. in Biochim. Biophys. Acta 775:169-174, 1984. Alternative industrial scalable processors include but are not limited to the Gaulin and Ranni Homogenizers (APV Gaulin/Rannie Homogenizers, St. Paul, Minn.).

Containers in which the propofol formulation can be stored include any container that is suitable for storing a pharmaceutical. Typical containers are made of glass and have been found to be inert to propofol. Treated glass containers such as siliconized glass containers are also useful. Plastic containers can also be used provided they are inert and/or are treated or coated to be inert. Suitable containers include vials, bottles, cartridges, syringes, pre-filled syringes and the like. The container is preferably sealed with a closure, such as, for example, a rubber stopper, plunger, lid, top or the like.

Suitable inert or non-reactive stoppers may be obtained from several commercial manufacturers. In general the preferred closures are made with inert, non-reactive materials with little to no leachables. Preferred closures also include those that are coated or treated with inert materials such as siliconized polymer or Teflon/fluoropolymer coated/treated closures. By way of example and not in limitation of the present invention, rubber closures that are suitable in the present invention include bromobutyl rubber, chlorobutyl rubber, fluoropolymers, silicones, siliconized bromobutyl rubber, and siliconized chlorobutyl rubber, provided, as described, the closure is inert to propofol or it is treated or coated to be inert to propofol. For example, American Stelmi supplies elastomeric closures or stoppers such as the 6720/6722 (models C1624, C1474) bromobutyl rubber or 6900 chlorobutyl rubber, some of which are suitable for propofol formulations because their use does not result in the degradation of propofol. Stoppers from other companies are also useful, provided such stoppers do not cause the degradation of propofol. For example, West Pharmaceutical makes elastomeric closures such as its 4400 series including 4416/50 gray butyl, 4405/50 gray butyl, 4416/50 gray butyl with Silicone, 4432/50 gray butyl, 4432/50 gray butyl with Silicone, 4432/50 gray butyl with Teflon, 4432/50 gray butyl with Silicone/Teflon, 4416/50 gray butyl with Teflon, 4405/50 gray butyl with Teflon, 4416/50 gray butyl, and also 1535 Red, PEP, and 8312/43 clear. Alternate closures from other manufacturers such as Helvoet Pharma are also suitable for use for closures for propofol formulations provided they do not cause degradation or loss in potency of propofol formulations.

Non-reactive, non-elastomeric closures are also useful. For example, non-rubber closures include metal closures, and plastics such as polyethylene, polypropylene, nylon, polyurethane, polyvinylchloride, polyacrylates, polycarbonates, and the like that themselves do not cause degradation to propofol or that are treated or coated so as not to cause degradation of propofol.

The following examples illustrate, but do not limit, the invention described above.

Example 1

Propofol-albumin compositions containing no solvent and no added surfactant. An emulsion containing 3% (by weight) of propofol was prepared as follows. The aqueous phase was prepared by adding human serum albumin (3% by weight) into water for injection and stirred until dissolved. The aqueous phase was passed through a filter (0.2 µm filter). The oil phase consists of neat propofol (3% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; Glycerol 2.25%; water for injection q.s. to 100; pH 5-8.

Example 2

Propofol-albumin compositions containing low solvent and no added surfactant. An emulsion containing 0.13% (by weight) of propofol was prepared as follows. The aqueous phase was prepared by adding human serum albumin (3% by weight) into water for injection and stirred until dissolved. The aqueous phase was passed through a filter (0.2 µm filter). The oil phase consists of propofol (0.13% by weight) and methanol (3%). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The emulsion is evaporated at reduced pressure to remove methanol. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; Glycerol 2.25%; water for injection q.s. to 100; pH 5-8.

Example 3

Propofol-albumin compositions containing no oil and with Tween 80 surfactant. An emulsion containing 1% (by weight)

of propofol was prepared as follows. The aqueous phase was prepared by adding human serum albumin (3% by weight) into water for injection and stirred until dissolved. The aqueous phase was passed through a filter (0.2 μm filter). Surfactant, e.g., Tween 80 (0.5%), was added to aqueous phase. The oil phase consisted of neat propofol (1% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen.

Formulations with the following general ranges of components (weight %) for such propofol compositions were prepared as follows: Propofol 0.5-5%; human serum albumin 0.01-3%; Tween 80 0.1-2%; Glycerol 2.25%; water for injection q.s. to 100; pH 5-8.

Example 4

Propofol-albumin compositions containing no oil and with Vitamin E-TPGS surfactant. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., Vitamin E TPGS (0.5%), was added to aqueous phase. The oil phase consisted of neat propofol (1% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion is filtered (0.2 μm filter) and stored under nitrogen.

Formulations with the following general ranges of components (weight %) for such propofol compositions were prepared as follows: Propofol 0.5-5%; human serum albumin 0.01-3%; Vitamin E-TPGS 0.1-2%; Glycerol 2.25%; water for injection q.s. to 100; pH 5-8.

Example 5

Propofol-albumin compositions containing no oil and with lecithin surfactant. An emulsion containing 1% (by weight) of propofol was prepared as follows. The aqueous phase was prepared by adding human serum albumin (3% by weight) into water for injection and stirred until dissolved. The aqueous phase was passed through a filter (0.2 μm filter). Surfactant, e.g., egg or soy lecithin (0.12%), was added to propofol. The oil phase consists of neat propofol (1% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen.

Formulations with the following general ranges of components (weight %) for such propofol compositions were prepared as follows: Propofol 0.5-10%; human serum albumin 0.01-5%; egg or soy lecithin 0.1-5%; Glycerol 2.25%; water for injection q.s. to 100; pH 5-8.

Example 6

Propofol-albumin compositions containing no oil and with lecithin surfactant. An emulsion containing 1-10% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., egg or soy lecithin (3.3%), was added to propofol. The oil phase consists of neat propofol (10% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen. The formulation was also diluted with additional aqueous phase to obtain suitable propofol concentrations, i.e., 1%, 2% and 5% in addition to the 10% formulation. All of these formulations were found to be stable. Adjustment of pH was made as necessary with standard pH modifiers. Thus, a wide range of propofol concentrations at 10% and below were prepared by this method. Formulations with the following general ranges of components (weight %) for such propofol compositions were prepared as follows: Propofol 0.5-10%; human serum albumin 0.01-5%; egg or soy lecithin 0.1-5%; Glycerol 2.25%; water for injection q.s. to 100; pH 5-8.

Example 7

Propofol-albumin compositions containing no oil and with Pluronic F127 surfactant. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., pluronic F127 (1.5%), was added to the aqueous phase. The oil phase consisted of neat propofol (10% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen. The formulation was also diluted to obtain suitable propofol concentrations e.g., 1%-5%.

Formulations with the following general ranges of components (weight %) for such propofol compositions were prepared as follows: Propofol 0.5-10%; human serum albumin 0.01-5%; pluronic F127 0.1-5%; Glycerol 2.25%; water for injection q.s. to 100; pH 5-8.

Example 8

Propofol-albumin compositions containing oil and lecithin. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-0.6%; Glycerol 2.25%; water for injection q.s. to 100; pH 5-8.

Example 9

Propofol-albumin compositions containing oil (2%) and egg lecithin (0.3%). An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 µm filter). The oil phase was prepared by dissolving egg lecithin (0.3% by weight) and propofol (1% by weight) into soybean oil (2% by weight) at about 50° C.-60° C. and stirred until dissolved. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-0.6%; Glycerol 2.25%; water for injection q.s. to 100; pH 5-8.

Example 10

Propofol-albumin compositions containing 1% oil. An emulsion containing 1% (by weight) of propofol was prepared as follows. The aqueous phase was prepared by adding glycerol (2.25% by weight) and human serum albumin (3% by weight) into water for injection and stirred until dissolved. The aqueous phase was passed through a filter (0.2 µm filter). The oil phase was prepared by dissolving propofol (1% by weight) into soybean oil (1% by weight) and stirred until dissolved. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; Glycerol 2.25%; water for injection q.s. to 100; pH 5-8.

Example 11

Propofol-albumin compositions containing 5% oil and lecithin. An emulsion containing 1% (by weight) of propofol was prepared as follows. The aqueous phase was prepared by adding glycerol (2.25% by weight) and human serum albumin (3% by weight) into water for injection and stirred until dissolved. The aqueous phase was passed through a filter (0.2 µm filter). The oil phase was prepared by dissolving egg lecithin (0.5% by weight) and propofol (1% by weight) into soybean oil (5% by weight) and chloroform (3% by weight) and stirred until dissolved. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The emulsion was evaporated under reduced pressure to remove the chloroform. The final emulsion was filtered (0.2 µm filter) and stored under nitrogen. Chloroform levels in the final formulation were in the acceptable range for parenteral administration of the propofol formulation.

Formulations with the following general ranges of components (weight %) for such propofol compositions were prepared as follows: Propofol 0.5-5%; human serum albumin 0.01-3%; soybean oil 0.5-6.0%; egg lecithin 0.1-0.6%; Glycerol 2.25%; water for injection q.s. to 100; pH 5-8.

Example 12

Propofol compositions containing 3% oil and lecithin (0.4%) with pH 7-8. An emulsion containing 1% (by weight) of propofol was prepared as follows. The aqueous phase was prepared by adding glycerol (2.25% by weight) into water for injection and stirred until dissolved. The aqueous phase pH was adjusted to pH 7-8 by addition of dilute hydrochloric acid or sodium hydroxide. The aqueous phase was passed through a filter (0.2 µm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 µm filter) and stored under nitrogen.

Formulations with the following general ranges of components (weight %) for such propofol compositions were prepared as follows: Propofol 0.5-5%; soybean oil 0.5-6.0%; egg lecithin 0.1-1.2%; Glycerol 2.25%; water for injection q.s. to 100; pH 5-8. Other conventional surfactants such as vitamin E (TPGS), Tween 80 and Pluronic F127 were also used.

In general pH adjustment for different formulations of propofol was done either prior to emulsification or after the homogenization process.

Example 13

Propofol compositions containing 3% oil and lecithin (0.4%) with pH 6-7. An emulsion containing 1% (by weight) of propofol was prepared as follows. The aqueous phase was prepared by adding glycerol (2.25% by weight) into water for injection and stirred until dissolved. The aqueous phase pH was adjusted to pH 6-7 by addition of dilute hydrochloric acid or sodium hydroxide. The aqueous phase was passed through a filter (0.2 µm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 µm filter) and stored under nitrogen.

Formulations with the following general ranges of components (weight %) for such propofol compositions were prepared as follows: Propofol 0.5-5%; soybean oil 0.5-6.0%; egg lecithin 0.1-1.2%; Glycerol 2.25%; water for injection q.s. to 100; pH 5-8. Other conventional surfactants such as vitamin E (TPGS), Tween 80 and Pluronic F127 were also used.

Example 14

Propofol compositions containing no oil and with Tween 80 Surfactant. An emulsion containing 1% (by weight) of propofol was prepared as follows. The aqueous phase was prepared by adding glycerol (2.25% by weight) into water for injection and Tween 80 (0.5%) and stirred until dissolved. The aqueous phase was passed through a filter (0.2 μm filter). The oil phase consists of neat propofol (1% by weight). The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion is filtered (0.2 μm filter) and stored under nitrogen.

Formulations with the following general ranges of components (weight %) for such propofol compositions prepared are as follows: Propofol 0.5-5%; Tween 80 0.1-2%; Glycerol 2.25%; water for injection q.s. to 100; pH 5-8.

Example 15

Propofol-albumin compositions containing oil (3%) and lecithin (0.4%) with pH 7-8. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 7-8 by addition of dilute sodium hydroxide. The aqueous phase was passed through a filter (0.2 μm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 μm filter) and stored under nitrogen.

Formulations with the following general ranges of components (weight %) for such propofol compositions prepared are as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 16

Propofol-albumin compositions containing oil (3%) and lecithin (0.4%) with pH 6-7. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 6-7 by addition of dilute hydrochloric acid. The aqueous phase was passed through a filter (0.2 μm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 μm filter) and stored under nitrogen.

Formulations with the following general ranges of components (weight %) for such propofol compositions prepared are as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 17

Propofol-albumin compositions containing oil (3%) and lecithin (0.7%) with pH 6-7. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 6-7 by addition of dilute hydrochloric acid. The aqueous phase was passed through a filter (0.2 μm filter). The oil phase was prepared by dissolving egg lecithin (0.7% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 μm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 18

Propofol-albumin compositions containing oil (3%) and lecithin (0.2%) with pH 6-7. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 6-7 by addition of dilute hydrochloric acid or other appropriate agent. The aqueous phase was passed through a filter (0.2 μm filter). The oil phase was prepared by dissolving egg lecithin (0.2% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 μm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 19

Propofol-albumin compositions containing oil (3%) and lecithin (0.2%) with pH 7-8. An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 7-8 by addition of dilute sodium hydroxide. The aqueous phase was passed through a filter (0.2 µm filter). The oil phase was prepared by dissolving egg lecithin (0.7% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 20

Propofol-albumin compositions containing oil (6%) and lecithin (0.8%) with pH 7-8. An emulsion containing 2% (by weight) of propofol was prepared as follows. The aqueous phase was prepared by adding glycerol (2.25% by weight) and human serum albumin (0.5% by weight) into water for injection and stirred until dissolved. The aqueous phase pH was adjusted to pH 7-8 by addition of dilute sodium hydroxide. The aqueous phase was passed through a filter (0.2 µm filter). The oil phase was prepared by dissolving egg lecithin (0.8% by weight) and propofol (2% by weight) into soybean oil (6% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 µm filter) and stored under nitrogen. This formulation was also further diluted with the aqueous phase to obtain a 1% propofol emulsion. Both the 1% and the 2% formulations were found to be satisfactory.

Formulations with the following general ranges of components (weight %) for such propofol compositions were prepared as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 21

Propofol-albumin compositions containing oil and lecithin added to aqueous phase. An emulsion containing 1% (by weight) of propofol was prepared as follows. The aqueous phase was prepared by adding glycerol (2.25% by weight), and lecithin (0.4%) and heated 40-60° C. to obtain a dispersion. Human serum albumin (0.5% by weight) was added into the cooled dispersion and stirred until dissolved. The oil phase was prepared by dissolving propofol (1% by weight) into soybean oil (3% by weight) and stirred until dissolved. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 µm filter) and stored under nitrogen.

Formulations with the following general ranges of components (weight %) for such propofol compositions were prepared as follows: Propofol 0.5-5%; human serum albumin 0.01-3%; soybean oil 0.5-6.0%; egg lecithin 0.1-1.2%; Glycerol 2.25%; water for injection q.s. to 100; pH 5-8.

Example 22

Propofol Compositions Containing Oil (3%) and Lecithin (0.4%) with pH 7-8.5

An emulsion containing 1% (by weight) of propofol was prepared as follows. The aqueous phase was prepared by adding glycerol (2.25% by weight) into water for injection and stirred until dissolved. The aqueous phase pH was adjusted to pH 7-8.5 by addition of dilute sodium hydroxide. The aqueous phase was passed through a filter (0.2 µm filter). The oil phase was prepared by dissolving egg lecithin (0.4% by weight) and propofol (1% by weight) into soybean oil (3% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 µm filter) and stored under nitrogen or argon.

Formulations with the following general ranges of components (weight %) for such propofol compositions were prepared as follows: Propofol 0.5-5%; soybean oil 0.5-6.0%; egg lecithin 0.1-1.2%; Glycerol 2.25%; water for injection q.s. to 100; pH 5-8.5.

Example 23

Propofol Compositions Containing Oil (5%) and Lecithin (0.8%) with pH 7-8.5

An emulsion containing 1% (by weight) of propofol was prepared as follows. The aqueous phase was prepared by adding glycerol (2.25% by weight) into water for injection and stirred until dissolved. The aqueous phase pH was adjusted to pH 7-8.5 by addition of dilute sodium hydroxide. The aqueous phase was passed through a filter (0.2 µm filter). The oil phase was prepared by dissolving egg lecithin (0.8% by weight) and propofol (1% by weight) into soybean oil (5% by weight) at about 50° C.-60° C. and stirred until dissolved. The oil phase was added to the aqueous phase and homogenized at 10,000 RPM for 5 min. Further pH adjustment using either acid or base was performed at this stage. The crude emulsion was high pressure homogenized at 20,000 psi and recirculated for up to 15 cycles at 5° C. Alternately, discrete passes through the homogenizer were used. Final pH adjustment if necessary was performed at this stage. The final emulsion was filtered (0.2 μm filter) and stored under nitrogen or argon.

Formulations with the following general ranges of components (weight %) for such propofol compositions were prepared as follows: Propofol 0.5-5%; soybean oil 0.5-6.0%; egg lecithin 0.1-1.2%; Glycerol 2.25%; water for injection q.s. to 100; pH 5-8.5.

Example 24

Oil-Free Propofol Compositions Containing Lecithin with pH 7-8.5

An emulsion containing 1-10% (by weight) of propofol was prepared as follows. The aqueous phase was prepared by adding glycerol (2.25% by weight) into water for injection and stirred until dissolved. The aqueous phase pH was adjusted to pH 7-8.5 by addition of dilute sodium hydroxide. A suitable buffer could be added into the aqueous phase if necessary. The aqueous phase was passed through a filter (0.2 μm filter). Surfactant, e.g., egg or soy lecithin (3.3%), was added to propofol. The oil phase consisted of neat propofol (10% by weight). The oil phase was added to the aqueous phase and homogenized at 10,000 RPM for 5 min. Further pH adjustment was performed as necessary. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen. The formulation was also diluted with additional aqueous phase to obtain suitable propofol concentrations, i.e., 1%, 2% and 5% in addition to the 10% formulation. All of these formulations were found to be stable. Adjustment of pH was made as necessary with standard pH modifiers. Thus, a wide range of propofol concentrations at 10% and below were prepared by this method. Formulations with the following general ranges of components (weight %) for such propofol compositions were prepared as follows: Propofol 0.5-10%; egg or soy lecithin 0.1-5%; Glycerol 2.25%; water for injection q.s. to 100; pH 5-8.5.

Example 25

Test for Bacterial Inhibition of Propofol Formulations

The objective of these tests was to determine the growth inhibition of microorganisms in different propofol formulations prepared as above. Approximately 100-200 colony forming units (CFU) per ml of four standard U.S.P. organisms *E. coli* (ATCC 8739), *S. aureus* (ATCC 6538), *C. albicans* (ATCC 10231) and *P. aeruginosa* (ATCC 9027) for preservative tests were inoculated in each formulation batch samples and incubated at 25° C.±1° C. The viable count of the test organism was determined at 0 hours, 24 hours and 48 hours after inoculations. Not more than 10-fold increase in growth of microorganisms at 24 hours after microbial contamination indicates the formulation is effective in inhibition of growth.

About 100-600 μL (approx. 100-200 CFU/ml) of each strain were inoculated into 2 ml of each tested batch sample tube (duplicated for each sample) and 2 ml TSB as control. Tryptic Soy Agar (TSA) plates were inoculated with 10% of the samples (20 drops of a 10 μL sterile disposable loop), duplicated for each sample. The TSA plates were inoculated aerobically at 25° C.±1° C. in the temperature controlled incubator. The colony count of the test organism and the CFU/ml were determined at 0 hour, 24 hours and 48 hours post microbial inoculation. The ratio of 24 hours counts vs. 0 hour counts and ratio of 48 hours counts vs. 0 hour counts were determined to evaluate the effectiveness in inhibition of microbial growth. Results with a ratio less than 10 indicated that the tested sample had the inhibition effect on the microbial growth.

The antimicrobial effects of the propofol invention compositions are summarized in the following tables.

TABLE 1

| Formulation Description | | | Microbial Growth against *E. coli* Ratios of CFU relative to 0 hr | |
|---|---|---|---|---|
| pH | % Oil | % Lecithin | 24 hr | 48 hr |
| 6.2 | 3 | 0.7 | 0 | 0 |
| 6.1 | 3 | 0.2 | N/D | N/D |
| 7.93 | 3 | 0.2 | N/D | N/D |
| 7.5 | 3 | 0.4 | 0 | 0 |
| 6 | 3 | 0.4 | 0 | 0 |
| 7.6 | 3 | 0.4 | 0.64 | 0 |
| 7.2 | 6 | 0.8 | N/D | N/D |

TABLE 2

| Formulation Description | | | Microbial Growth against *S. aureus* Ratios of CFU relative to 0 hr | |
|---|---|---|---|---|
| pH | % Oil | % Lecithin | 24 hr | 48 hr |
| 6.2 | 3 | 0.7 | N/D | N/D |
| 6.1 | 3 | 0.2 | N/D | N/D |
| 7.93 | 3 | 0.2 | N/D | N/D |
| 7.5 | 3 | 0.4 | 0.52 | 1.41 |
| 6 | 3 | 0.4 | N/D | N/D |
| 7.6 | 3 | 0.4 | 0.67 | 0.4 |
| 7.2 | 6 | 0.8 | 0 | 0 |

TABLE 3

| Formulation Description | | | Microbial Growth against *C. albicans* Ratios of CFU relative to 0 hr | |
|---|---|---|---|---|
| pH | % Oil | % Lecithin | 24 hr | 48 hr |
| 6.2 | 3 | 0.7 | N/D | N/D |
| 6.1 | 3 | 0.2 | 0.04 | 1 |
| 7.93 | 3 | 0.2 | 0.01 | 0.03 |
| 7.5 | 3 | 0.4 | 0.28 | 0.34 |
| 6 | 3 | 0.4 | 1.29 | 0.57 |
| 7.6 | 3 | 0.4 | 0.47 | 0.44 |
| 7.2 | 6 | 0.8 | 0 | 0 |

TABLE 4

| Formulation Description | | | Microbial Growth against *P. aeruginosa* Ratios of CFU relative to 0 hr | |
|---|---|---|---|---|
| pH | % Oil | % Lecithin | 24 hr | 48 hr |
| 6.2 | 3 | 0.7 | N/D | N/D |
| 6.1 | 3 | 0.2 | N/D | N/D |
| 7.93 | 3 | 0.2 | N/D | N/D |
| 7.5 | 3 | 0.4 | N/D | 0.58 |
| 6 | 3 | 0.4 | N/D | 3.67 |
| 7.6 | 3 | 0.4 | 0 | 0 |
| 7.2 | 6 | 0.8 | N/D | N/D |

The variation of pH between about pH 6 to pH 8 did not have any significant impact on the bacterial growth profile. In addition, a lecithin range of 0.2-0.7 did not impact bacterial growth. An oil concentration in the range of 3-6% did not significantly impact bacterial growth. In the case of all the formulations above it was noted that the strains of bacteria tested did not show an increase greater than 10 fold in 24 or 48 hours under the experimental conditions tested.

Example 26

Presence of Protein as Part of the Stabilizing Layer in Propofol Formulations

Propofol-albumin compositions described above containing no oil or low amount of solvent (oil) are stabilized by the presence of albumin as well as the surfactant if such surfactant is present. It is well recognized that a surfactant can stabilize an emulsion by forming a stabilizing layer at the surface of the oil phase or droplet phase of the emulsion. In the case of invention compositions containing albumin, it is found that albumin is also present on the droplets of the oil phase of the emulsion. Two propofol formulations (a) containing no oil, but with propofol (1%), lecithin (0.33%) and albumin (0.5%) and (b) containing 3% soybean oil and propofol (1%), lecithin (0.4%) and albumin (0.5%) were centrifuged at 14000×g to separate the aqueous and oil phases. The oil phase was removed, washed, recentrifuged and separated twice. The separated oil phases were then resuspended in water for injection and the protein content analyzed by using size exclusion chromatography on an HPLC. Albumin was detected in these samples at a wavelength of 228 nm and 280 nm. The total albumin measured in the droplet phase of the emulsion was at least 1-8% of the albumin in the formulation. This indicated that albumin was adsorbed on the droplets of neat propofol or soybean oil/propofol as part of the stabilizing layer. Thus the stabilizing layer in such invention formulations comprises both the surfactant (e.g., lecithin) as well as the protein (albumin).

Example 27

Binding of Propofol to Albumin

Addition of albumin to propofol formulations was surprisingly found to bind the free propofol in these formulations. The binding of propofol to albumin was determined as follows. Solubility of propofol was tested in water and in solutions containing albumin. 250 µL of propofol was added to 10 ml of the water or albumin solution and stirred for 2 hours in a scintillation vial. The solution was then transferred to a 15 ml polyethylene centrifuge tube and kept at 40° C. for about 16 hours. Samples of water and albumin solutions were assayed for propofol. Solubility of propofol in water was determined to be 0.12 mg/ml. Solubility of propofol in albumin solutions was dependent on the concentration of albumin and increased to 0.44 mg/ml when the albumin concentration was 2% (20 mg/ml). The solutions were ultrafiltered through a 30 kD MWCO filter and the filtrates assayed for propofol by HPLC. It was found that for the propofol/water solution, 61% of the propofol could be recovered in the filtrate whereas for the propofol/albumin solution, only 14% was recovered in the filtrate indicating a substantial binding of propofol with albumin. Based on this result, addition of albumin to formulations of propofol result in a decrease in the amount of free propofol due to albumin binding of the propofol. This can result in a decrease in side effects of administration such as venous irritation, pain, etc.

Example 28

Reduction of Free Propofol in Formulations Containing Albumin

To further test the binding of free propofol to albumin in an emulsion formulation of propofol, albumin was added to Diprivan® at different concentrations (0.5%, 2% and 5%). The amount of free propofol was measured as described above by ultrafiltration of the samples followed by HPLC assay for free propofol. The concentrations of free propofol in the albumin containing formulations were compared a control sample (0% albumin) of albumin-free Diprivan®. Each of the tests was done in triplicate. The concentrations of free propofol in the 0.5%, 2% and 5% albumin-containing Diprivan® samples respectively were reduced by 22%, 56% and 78% respectively. Similar results were obtained for invention formulations of propofol. Once again, based on these results, the presence of albumin in invention formulations of propofol results in a decrease in the amount of free propofol due to albumin binding of the propofol. This in turn results in a decrease in side effects of administration such as venous irritation, pain, etc.

Example 29

Clinical Trials to Determine Pain

A randomized, double-blind clinical trial was conducted to compare adverse skin sensations of the propofol formulations of embodiments of the invention which contain albumin with that of a commercially available propofol formulation, Diprivan®. Trials were conducted in compliance with Good Clinical Practices and "informed consent" was taken from the subjects. Adult human subjects of either sex were eligible for participation if they had unbroken, apparently normal skin on the dorsal side of their hands.

The formulations originally stored in a refrigerator were brought to room temperature and then 10 µL of the formulations was placed slowly on the back side of both the hands of a subject simultaneously. The overall reaction and feel on their hands for the formulations were noted.

| Order of | % of subjects with Albumin-Propofol sensation | | % of subject with Diprivan ® sensation | |
|---|---|---|---|---|
| | Mild warm or stinging or biting | No sensation | Mild warm or stinging or biting | No sensation |
| a test on a subject $1^{st}$ incidence | 0.0 | 100.0 | 75 | 25 |

Example 30

Anesthetic Effect of Propofol Formulations Containing Low and No Oil in Rats

The anesthetic effect and potency of the propofol formulations in accordance with embodiments of the present invention and containing 0% and 3% soybean oil were compared with those of propofol in 10% soybean oil emulsion (Diprivan®) in rats. Male Sprague-Dawley rats were assigned to six groups (n=10 in each) to receive single i.v. bolus doses of the formulations. Righting reflex and response to tail clamping were assessed at periodic intervals. The loss of righting reflex and loss of response to tail clamp were used as measures of hypnosis and antinocifensive response, respectively. Nocifensive stimuli were tested by application of a 2-cm serrated alligator clip to the middle third of the tail. Data were analyzed with repeated measures ANOVA.

There were no significant differences in the number of rats who exhibited loss of righting reflex or loss of response to tail clamp after i.v. injection of a 10 mg/kg dose of the three preparations of propofol. However, at 5 mg/kg dose, significantly greater number of rats who received oil-free preparation exhibited loss of righting reflex and loss of response to tail clamp at 2 min compared to those who received Diprivan®. Intravenous injection of the vehicle did not affect righting reflex or tail clamp response.

This study demonstrated that decreasing the concentrations of soybean oil did not affect the anesthetic properties of propofol in rats. The transient increase of activity seen with 5 mg/kg dose of the oil-free preparation may be attributed to the increased availability of free drug due to absence of oil. Decreasing or eliminating soybean oil from propofol is beneficial in preventing hyperlipidemia seen with current formulations of propofol.

Example 31

Method for Testing Compatibility of Propofol Emulsions

The following method was used for accelerated testing of propofol emulsions and the effect of different closures on propofol degradation or potency. Propofol emulsions (1-5 ml) were added into glass vials (5-20 ml) or other suitable vials, sealed with appropriate closures to be tested and mounted on a multi-arm reciprocating shaker device [Burrell Scientific, Model 75]. The device is capable of agitating the vials in a reciprocating manner with control over the amplitude of shaking stroke. The vials were agitated at a frequency of about 300-400 cycles/minute. The samples were mounted on the shaker at room temperature for 16 hours. An HPLC assay of the propofol samples before and after the treatment determined if there was a loss in the potency or concentration of propofol in the formulations. This method allowed the rapid testing of closure compatibility with different propofol formulations as well as the emulsion stability. Closures tested in this study were standard serum vial closures such as those prepared from bromobutyl rubber, chlorobutyl rubber, rubber closures with coated Teflon, or fluorotec closures, siliconized closures, closures for scintillation vials (non-rubber, aluminium/metal backing). Such closures/vials were obtained from sources such as Wheaton, Stelmi, West, Dalkyo, Helvoet.

In the examples below, the following stoppers were used.

| Closure code | Closure type | Composition type |
| --- | --- | --- |
| Rubber 1 | Rubber | Bromobutyl rubber |
| Rubber 2 | Stelmi 6720 (C1624) | Bromobutyl rubber |
| Rubber 3 | Stelmi 6720 (C1474) | Bromobutyl rubber |
| Rubber 4 | Stelmi 6900 | Chlorobutyl rubber |
| Teflon face 1 | West 4405/50 Teflon | Butyl rubber with fluoropolymer |
| Teflon face 2 | West 4432/50 Teflon | Butyl rubber with fluoropolymer |
| Teflon face 3 | GC teflon seal | fluoropolymer |
| Metal face | Scintillation vial cap | Metal |

Example 32

Rubber Closure Vs. Coated/Inert Closure for Oil-Free Propofol Formulations

Propofol formulations devoid of any oils were prepared as described above. These formulations contained approximately 1%(w/v) propofol. Several vials of samples with different closures were prepared. The formulations were loaded on the shaking device as described above for 16 hours. The HPLC assays for propofol content post-shaking were compared to the original (control) samples to obtain the % recovery of propofol. The results are shown in the table below.

| Composition of Formulations | | | | | Propofol |
| --- | --- | --- | --- | --- | --- |
| % Soybean Oil | % lecithin | % albumin | % propofol | Closure Type | conc % of Control |
| 0 | 0.33 | 0.5 | 1 | Rubber 1 | 23.2 |
| 0 | 0.33 | 0.5 | 1 | Rubber 2 | 35.9 |
| 0 | 0.33 | 0.5 | 1 | Rubber 3 | 45.0 |
| 0 | 0.33 | 0.5 | 1 | Rubber 4 | 44.1 |
| 0 | 0.33 | 0.5 | 1 | Teflon face 1 | 101.0 |
| 0 | 0.33 | 0.5 | 1 | Teflon face 3 | 97.9 |
| 0 | 0.33 | 0.5 | 1 | Metal face | 100.0 |
| 0 | 0.33 | 0 | 1 | Rubber 1 | 27.3 |
| 0 | 0.33 | 0 | 1 | Teflon face 2 | 99.9 |

A substantial drop of propofol concentration was seen for closures Rubber 1-4 indicating incompatibility of the closure material and propofol, leading to the degradation of propofol and loss of potency of the formulation. Only 23-45% of the original propofol concentration was recovered for these rubber closures. In case of the Teflon faced stoppers and the metal-faced stopper, close to 100% of the original potency of propofol was retained. This effect was independent of whether the formulation contained albumin or not. This surprising finding indicates that propofol formulations containing no oil must be stored in containers with either closures that are coated with inert materials or made entirely of inert materials to avoid a potency drop or degradation of propofol.

Example 33

Rubber Closure Vs. Coated/Inert Closure for 3% Oil Propofol Formulations

Propofol formulations containing 3% soybean oil were prepared as described above. These formulations contained approximately 1% (w/v) propofol. Several vials of samples with different closures were prepared. The formulations were loaded on the shaking device as described above for 16 hours. The HPLC assays for propofol content post-shaking were compared to the original (control) samples to obtain the recovery of propofol. The results are shown in the table below.

| Composition of Formulations | | | | | Propofol |
| --- | --- | --- | --- | --- | --- |
| % Soybean Oil | % lecithin | % albumin | % propofol | Closure Type | conc % of Control |
| 3 | 0.4 | 0.5 | 1 | Rubber 1 | 52.9 |
| 3 | 0.4 | 0.5 | 1 | Rubber 2 | 93.4 |
| 3 | 0.4 | 0.5 | 1 | Rubber 3 | 99.9 |
| 3 | 0.4 | 0.5 | 1 | Rubber 4 | 95.8 |

| Composition of Formulations | | | | | Propofol |
|---|---|---|---|---|---|
| % Soybean Oil | % lecithin | % albumin | % propofol | Closure Type | conc % of Control |
| 3 | 0.4 | 0.5 | 1 | Teflon face 1 | 101.1 |
| 3 | 0.4 | 0.5 | 1 | Teflon face 2 | 103.3 |

One of the three rubber closures used (Rubber 1) showed a loss in potency of about 47% of the propofol. The Rubber 2, 3 and 4 as well as the Teflon face 1 and 2 showed either no loss in propofol potency or marginal (<7%) loss in propofol potency. Compared to the oil free formulations, a surprisingly lesser amount of potency loss was observed with the same rubber closures when the formulations contained 3% oil. This surprising finding indicates that soybean oil in propofol formulations protects the propofol from potential degradation. However, certain rubber compositions may still cause degradation of the propofol, and even with propofol compositions which include soybean oil, containers with inert closures are preferred.

Example 34

Effect of Oil Concentration on Propofol Potency with Rubber Closures

Propofol formulations containing 0, 2, 3, 5% soybean oil were prepared as described above. A 10% soybean oil formulation (Diprivan®) was also obtained for this study. These formulations all contained approximately 1% (w/v) propofol. Several vials of samples with rubber (Rubber 1) closures were prepared. The formulations were loaded on the shaking device as described above for 16 hours. The HPLC assays for propofol content post-shaking were compared to the original (control) samples to obtain the recovery of propofol. The results are shown in the table below.

| Composition of Formulations | | | | | Propofol |
|---|---|---|---|---|---|
| % Soybean Oil | % lecithin | % albumin | % propofol | Closure Type | conc % of Control |
| 10* | 1.2 | 0 | 1 | Rubber 1 | 99.3 |
| 5 | 0.8 | 0.2 | 1 | Rubber 1 | 82.9 |
| 3 | 0.4 | 0.5 | 1 | Rubber 1 | 52.9 |
| 0 | 0.33 | 0.5 | 1 | Rubber 1 | 23.2 |
| 0 | 0.33 | 0 | 1 | Rubber 1 | 27.3 |

*Commercially available Diprivan®.

The data shows that the oil in the formulation protected propofol from degradation. As the percent of oil in the formulation was decreased, the potency of propofol also decreased confirming that the oil had a protective effect on propofol. However at oil concentrations of 3% and 5%, an approximately 47% and 17% loss in propofol potency was noted indicating that an inert closure material was essential for formulations of propofol containing less than 10% oil.

Example 35

Rubber Closure v. Coated/Inert Closure for Albumin and Non-Albumin Propofol Formulations Propofol formulations devoid of oils were prepared as described above. These formulations contained approximately 1% (w/v) propofol. These formulations were prepared either with human albumin or without human albumin to elucidate if albumin had any effect on propofol degradation. Several vials of samples with different closures were prepared. The formulations were loaded on the shaking device as described above for 16 hours. The HPLC assays for propofol content post-shaking were compared to the original (control) samples to obtain the % recovery of propofol. The results are shown in the table below.

| Composition of Formulations | | | | | Propofol |
|---|---|---|---|---|---|
| % Soybean Oil | % lecithin | % albumin | % propofol | Closure Type | conc % of Control |
| 0 | 0.33 | 0.5 | 1 | Rubber 1 | 23.2 |
| 0 | 0.33 | 0.5 | 1 | Teflon face 1 | 101.0 |
| 0 | 0.33 | 0 | 1 | Rubber 1 | 27.3 |
| 0 | 0.33 | 0 | 1 | Teflon face 2 | 99.9 |

With each of the rubber closures tested, a substantial drop of propofol concentration was seen indicating incompatibility of the closure material. Only 23-27% of the original propofol concentration was recovered for the rubber closures. This effect was independent of whether the formulation contained albumin or not. In case of the Teflon faced stoppers, approximately 100% of the original potency of propofol was retained. This effect was independent of whether the formulation contained albumin or not. Thus, the presence of albumin in invention formulations did not affect the degradation of propofol.

Example 36

Effect of Additives Such as EDTA and Sodium Metabisulfite

Sodium metabisulfite and EDTA are both used in commercially available preparations of propofol containing 10% oil. To test if any of these additives provided a protective effect on propofol degradation in the accelerated testing described above, these additives were also tested in formulations of propofol containing no oil. Disodium EDTA was used at a concentration of 0.0055% (as in Diprivan® and sodium metabisulfite was added at a concentration of 0.1% (as in the Gensia-Sicor product). The results are tabulated below:

| Additive | Composition of Formulations | | | | Closure Type | Propofol conc % of Control |
|---|---|---|---|---|---|---|
| | % Soybean Oil | % lecithin | % albumin | % propofol | | |
| | 0 | 0.33 | 0.5 | 1 | Teflon face 1 | 101.0 |
| | 0 | 0.33 | 0 | 1 | Rubber 1 | 27.3 |
| | 0 | 0.33 | 0.5 | 1 | Rubber 1 | 25.0 |
| 0.0055% EDTA | 0 | 0.33 | 0.5 | 1 | Rubber 1 | 15.9 |
| 0.1% metabisulfite | 0 | 0.33 | 0.5 | 1 | Rubber 1 | 17.4 |

The results above indicated that commercial additives EDTA and sodium metabisulfite do not play a role in preventing propofol degradation if the closure is not inert to propofol. Therefore the presence of 10% oil in the commercial formulations appears to be the major protective factor for preventing propofol degradation in the absence of non-reactive or inert closures, as described herein.

Example 37

Shelf Stability of Propofol Formulations

Propofol formulations prepared as above were tested for shelf stability in serum vials stoppered with rubber closures of the type "Rubber 1." The different formulations were placed in stability chambers with a controlled environment of 40° C. and 75% relative humidity for up to two months. Propofol concentrations in the formulations were compared to their respective time zero values. Results are tabulated below:

| Composition of Formulations | | | | | |
|---|---|---|---|---|---|
| % Soybean Oil | % lecithin | % albumin | % propofol | Closure Type | Propofol conc % |
| 0 | 0.33 | 0.5 | 1 | Rubber 1 | 34.3* |
| 3 | 0.4 | 0.5 | 1 | Rubber 1 | 72.1 |
| 5 | 0.8 | 0.5 | 1 | Rubber 1 | 89.6 |
| 10 | 1.2 | 0 | 1 | Rubber 1 | 96.8 |

*data at 2 weeks, rest of data at 2 months

These results confirmed the degradation of propofol as a result of incompatibility with the rubber closures when vials containing different propofol samples were placed in a stability chamber at standard accelerated shelf-stability conditions. Surprisingly, the samples with higher amount of oil showed a greater degree of protection from degradation. There was minimal (within limits of experimental error) to no degradation in the sample containing 10% oil, but increasingly greater amounts of degradation, approximately 10% and 28% respectively for samples containing 5% and 3% oil and substantially higher degradation for the sample without oil. Since a similar result was obtained in the shaker test described above, it was concluded that the shaker test, for which results could be obtained within 24 hours, was a suitable surrogate for accelerated testing in conventional shelf-stability chambers, and confirmed the surprising and unexpected finding that inert or non-reactive container closures are essential to prevent propofol degradation or loss of propofol potency in propofol formulations with less than 10% oil.

What is claimed is:

1. A container storing an anesthetic, comprising:
a container sealed by a closure and storing an oil-in-water anesthetic emulsion or an anesthetic solution,
the anesthetic being from 0.1% to 10% by weight of the oil-in-water anesthetic emulsion or the anesthetic solution,
the container being made of a material that is inert to the anesthetic, and
the closure being made of siliconized bromobutyl rubber or siliconized chlorobutyl rubber, wherein:
a concentration of the anesthetic in the oil-in-water anesthetic emulsion or the anesthetic solution stored in the container following a predetermined time period is at least 93% of a concentration of the anesthetic in the oil-in-water anesthetic emulsion or the anesthetic solution before the oil-in-water anesthetic emulsion or the anesthetic solution is stored in the container, and
the closure is in contact with at least some of the oil-in-water anesthetic emulsion or the anesthetic solution when the container is sealed by the closure.

2. The container of claim 1, wherein the anesthetic is propofol.

3. The container of claim 1, wherein the container is selected from the group consisting of a vial, a bottle, a cartridge, a syringe, and a pre-filled syringe.

4. The container of claim 1, wherein the material that is inert to the anesthetic is glass.

5. The container of claim 4, wherein the glass is siliconized glass.

6. The container of claim 1, wherein the material that is inert to the anesthetic is plastic.

7. The container of claim 1, wherein the closure is selected from the group consisting of a stopper, a plunger, a lid, and a top.

8. The container of claim 1, wherein the closure is made of the siliconized bromobutyl rubber.

9. The container of claim 1, wherein the closure is made of the siliconized chlorobutyl rubber.

10. The container of claim 1, wherein the predetermined time period is 16 hours, and the concentration of the anesthetic in the oil-in-water anesthetic emulsion or the anesthetic solution stored in the container following 16 hours is at least 93% of a concentration of the anesthetic in the oil-in-water anesthetic emulsion or the anesthetic solution before the oil-in-water anesthetic emulsion or the anesthetic solution is stored in the container.

11. The container of claim 1, wherein the oil-in-water anesthetic emulsion further comprises a solvent.

12. The container of claim 11, wherein the solvent is less than 10% by weight of the oil-in-water anesthetic emulsion.

13. The container of claim 11, wherein the solvent is a water-immiscible solvent.

14. The container of claim 13, wherein the water-immiscible solvent is selected from the group consisting of soybean oil, safflower oil, cottonseed oil, corn oil, coconut oil, sunflower oil, arachis oil, castor sesame oil, orange oil, limonene oil, olive oil, hydrogenated castor oil, marine oil, fractionated oil, an ester of a medium-chain fatty acid, an ester of a long-chain fatty acid, a chemically modified palmitate, a glyceral ester, a polyoxyl, and mixtures thereof.

15. The container of claim 1, wherein the oil-in-water anesthetic emulsion further comprises a surfactant.

16. The container of claim 15, wherein the surfactant is selected from the group consisting of phosphatides, synthetic phospholipids, natural phospholipids, lecithins, ethoxylated ethers, ethoxylated esters, tocopherol polyethylene glycol stearate, polypropylene-polyethylene block co-polymers, polyvinyl pyrrolidone, polyvinylalcohol, and combinations thereof.

17. The container of claim 16, wherein the surfactant is selected from the group consisting of egg phosphatides, soya phosphatides, egg lecithins, soya lecithins, and combinations thereof.

18. The container of claim 1, wherein the container stores the oil-in-water anesthetic emulsion.

19. The container of claim 1, wherein the container stores the anesthetic solution.

20. A container storing an anesthetic, comprising:
a container sealed by a closure and storing an oil-in-water anesthetic emulsion or an anesthetic solution, the anesthetic being from 0.1% to 10% by weight of the oil-in-water anesthetic emulsion or the anesthetic solution, the container being made of a material that is inert to the anesthetic, and the closure being made of siliconized bromobutyl rubber or siliconized chlorobutyl rubber, wherein:

a concentration of the anesthetic in the oil-in-water anesthetic emulsion or the anesthetic solution stored in the container following a predetermined time period is at least 93% of a stating concentration of the anesthetic in the oil-in-water anesthetic emulsion or the anesthetic solution, and the closure is in contact with at least some of the oil-in-water anesthetic emulsion or the anesthetic solution when the container is sealed by the closure.

21. The container of claim 20, wherein the anesthetic is propofol.

* * * * *